United States Patent [19]
L'Esperance, Jr.

[11] Patent Number: 4,951,663
[45] Date of Patent: Aug. 28, 1990

[54] METHOD FOR ENHANCED STERILIZATION OF A LIVING-TISSUE AREA OF PROSPECTIVE SURGICAL INVASION

[75] Inventor: Francis A. L'Esperance, Jr., Englewood, N.J.

[73] Assignee: L'Esperance Medical Technologies, Inc., New York, N.Y.

[21] Appl. No.: 286,330

[22] Filed: Dec. 19, 1988

Related U.S. Application Data

[63] Continuation-in-part of Ser. No. 148,890, Jan. 27, 1988, Pat. No. 4,931,053.

[51] Int. Cl.$^5$ ............................................. A61N 5/06
[52] U.S. Cl. .................................. 128/395; 128/898; 128/897; 606/10; 606/13; 606/17
[58] Field of Search ...................... 128/303.1, 365, 397, 128/398, 362, 897, 898; 604/20; 606/2–10, 13–19

[56] References Cited

U.S. PATENT DOCUMENTS 4,651,734  3/1987  Oseroff ................................ 128/345

FOREIGN PATENT DOCUMENTS 266038   5/1988  European Pat. Off. ......... 128/303.1
2126717  3/1984  United Kingdom ............. 128/303.1

OTHER PUBLICATIONS

"Photoradiation Therapy for the Treatment of Malignant Tumors" by Dougherty et al; Cancer Research vol. 38 8/78 pp. 2628–2635.
"Selective Absorption of Ultraviolet Laser Energy by Duman Atherosclerotic Plaque Treated with Tetracycline" by Murphy-Chutorian Am. J. Cartology vol. 55, 5/1/85 pp. 1293–1297.

*Primary Examiner*—Lee S. Cohen
*Assistant Examiner*—David Shay
*Attorney, Agent, or Firm*—Hopgood, Calimafde, Kalil, Blaustein & Judlowe

[57] ABSTRACT

The invention contemplates laser-aseptic phototherapy, for enhanced sterilization of an area of prospective surgical invasion of living tissue, by first administering, intravenously, orally or otherwise as appropriate, a photosensitizing agent having the property, in the course of an acceptable period of time, of selective concentrated absorption in bacteria and other microorganisms such as those which exist at depth in hair follicles, and then, following lapse of the time period, applying laser irradiation to the area of prospective surgery, using a wavelength and power density selected for absorptive response by the photosensitive agent, whereby microorganisms are destroyed at and beneath the irradiated area.

38 Claims, 2 Drawing Sheets

METHOD FOR ENHANCED STERILIZATION OF A LIVING-TISSUE AREA OF PROSPECTIVE SURGICAL INVASION

RELATED CASE

This application is a continuation-in-part of copending application Ser. No. 148,980, filed Jan. 27, 1988 now U.S. Pat. No. 4,931,053.

BACKGROUND OF THE INVENTION

In one aspect, the invention relates to the use of laser radiation to promote or enhance vascular or other growth in a thus-irradiated local area of living body tissue, and in another aspect, the invention pertains to laser aseptic phototherapy.

In their paper, "Some New Findings on Retinal Irradiation by Krypton and Argon Lasers",* J. Marshall, et al. review the histopathology of the acute effects of krypton and argon laser radiation on the human retina, and these effects are related to their long-term pathology by observations on diabetics. Emphasis was on laser photocoagulation but some "surprising findings" were reported involving proliferation of vascular endothelial cells adjacent the reaction site. And in a later paper, "He-Ne Laser Stimulation of Human Fibroblast Proliferation and Attachment in Vitro",** coauthored by J. Marshall, laboratory studies are reported for laser-irradiated cultures of excised human tissues, wherein the irradiation source was a 1 mW helium-neon laser providing a coherent source at 633-nm, wherein the irradiation was chopped at 100 Hz, to provide a 50 percent duty cycle; for each experiment, a comparative run was made involving monochromatic incoherent light via a 640-nm interference filter (bandwidth 9 nm), adjusted for intensity comparable with that of laser delivery to an identical culture. The reported result was that, at 24 and at 48 hours after 15-minute exposure, the particular laser-irradiated cultures exhibited a significant increase in the number of cells in comparison with their respective non-irradiated controls, while no significant change in cell counts was observed between irradiated and control circuits in experiments with the incoherent source.

*  *Docum. Ophthal. Proc. Series*, Vol. 36, pp. 21-37, 1984, Dr. W. Junk Publishers, The Hague.

** *Lasers in the Life Sciences* 1(2), 1986 pp. 125-134, Harwood Academic Publishers GmbH.

In said application Ser. No. 148,980, two laser systems are described for enhanced vascular and other growth, and the added material of the present application pertains to use of the same or similar apparatus for laser aseptic phototherapy.

BRIEF STATEMENT OF THE INVENTION

It is an object of the invention to provide an improved method and means for in-vivo laser irradiation of living-body tissue.

It is a specific object to achieve the above object using perturbation effects induced by multiple beams of laser irradiation delivered to affected body tissue.

Another specific object is to achieve the above objects without inducing photocoagulation, photoopticaltissue breakdown, photovaporization, or photoablative decomposition of the affected body tissue and/or cells.

Still another specific object is to provide a biomedical sterilizing system which can destroy microorganisms in the dermis as well as in the epidermis and thus deter microbial re-emergence during and after surgery.

The invention achieves the foregoing objects by directing at least two beams of laser irradiation at an affected area of body tissue, wherein the irradiation (a) is of low-to-moderate intensity at tissue impingement and (b) is also of spectral wavelength that is preferably in the visible or in the infrared. Perturbations result in the affected cells either directly by reason of differences in the physical properties of the respective beams or indirectly by reason of interaction between the two beams at or near the situs of delivery to the affected body tissue. In presurgical use, the ingestion of certain photosensitizers enables selective destruction of microorganisms in reaction to penetrating laser irradiation.

DETAILED DESCRIPTION

The invention will be described in detail for presently preferred apparatus, in conjunction with the accompanying drawings, in which.

Figure 1:
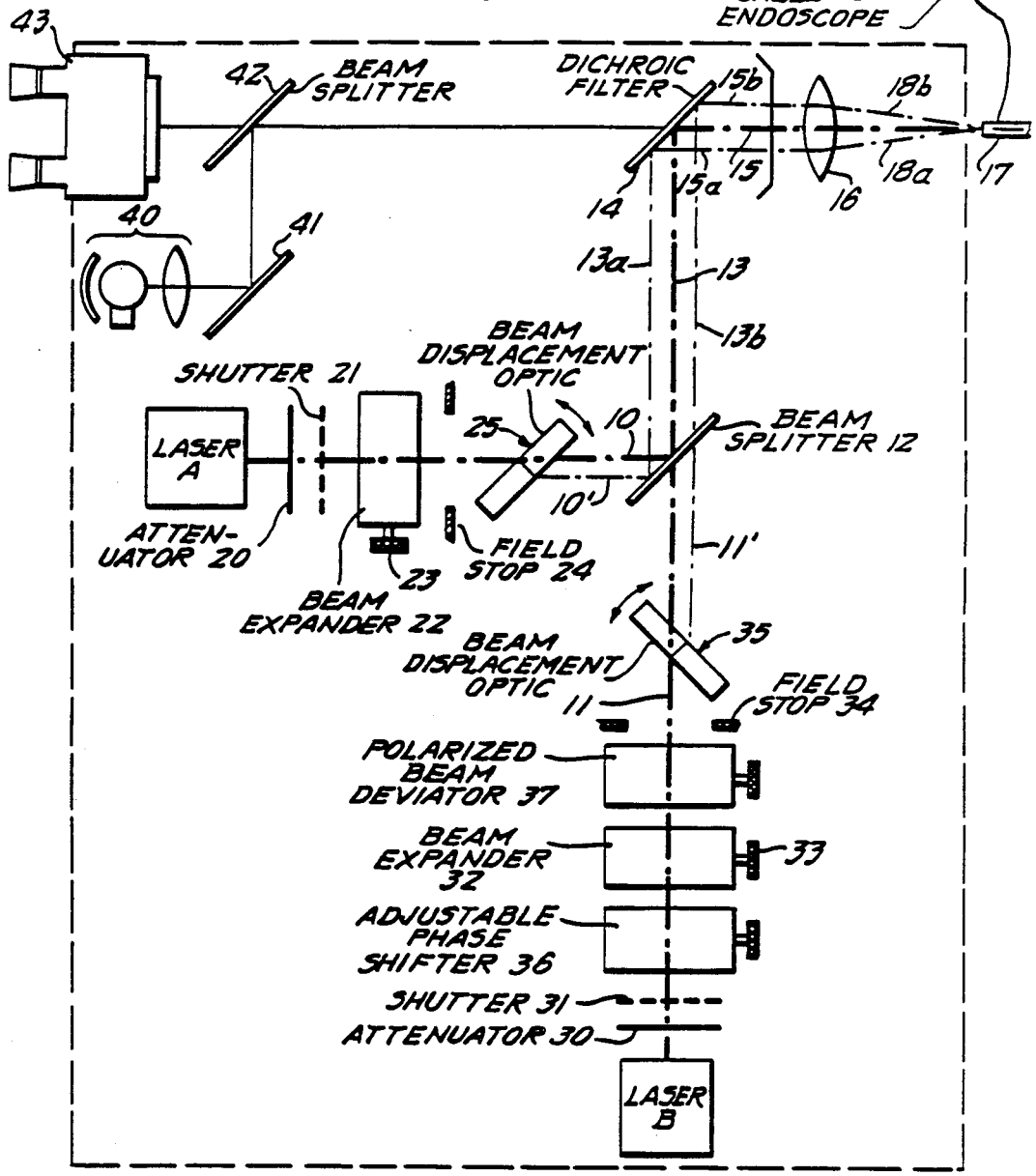
FIG. 1 is an optical diagram schematically indicating components of apparatus of the invention.

In FIG. 1, a first laser A delivers an output beam on a first optical axis 10, and a second laser B delivers an output beam on a second optical axis 11 which is orthogonally oriented for intersection and folded merger with axis 10 at a beam splitter 12. As a consequence, both laser beams utilize a common axis 13 of therapeutic energy delivery which, in the form shown, employs a dichroic filter 14 to fold projected laser energy onto a delivery axis 15. The delivered energy may be in the form of a collimated beam, producing a circular or otherwise configured spot at impact with living tissue to be irradiated; alternatively, as suggested by converginglens means 16, the laser energy may be converged to a lesser area for coupling to a fiber-optic delivery system 17, as in the case of an endoscope utilization.

Each of the lasers A, B preferably emits in the visible or in the infrared portion of the spectrum and at sufficiently low power, in terms of energy delivered to body tissue, thus avoiding coagulation of tissues and/or cells. Suitable and reasonably priced heliumneon, krypton and diode lasers are available for present purposes, and modes of use will determine particular selection.

To further facilitate particular desired modes of use, optical elements on axis 10 are shown to include attenuator means 20 (which may be selectively variable), shutter means 21 (which may be mechanical and electromagnetically actuated, or electro-optical and electronically actuated), a beam expander 22 (with manual means 23 for adjusting expansion), a field stop 24, and a beam-displacement optic 25 (having provision for its adjustable tilt with respect to axis 10, as suggested by double-headed arcuate symbolism). In similar fashion, optical elements on axis 11 are shown to include attenuator means 30, shutter means 31, a beam expander 32 (with adjustment means 33), a fixed stop 34, and an adjustable-tilt beam-displacement optic 35; in addition, the optical elements on axis 11 are seen to include adjustable phase-shifter means 36 to enable selective phase offset of the axis-10 beam with respect to the axis-11 beam (in the event that lasers A and B are identical), and means 37 for selective angular shifting of the polarization of one with respect to the other of beams 10–11. A suitable polarization-rotator product of Newport Corporation is identified by Catalog Number PR-550 for use in the visible spectrum, or by Catalog Number PR-950 for use in the near-infrared (700 to 1200-nm).

Figure 2:
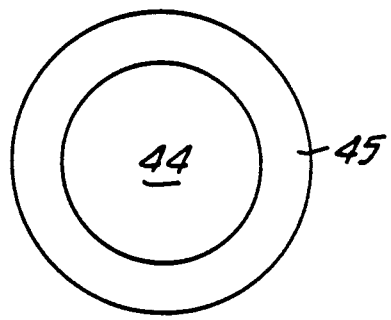
FIG. 2 is an enlarged diagram indicative of a beam-delivery embodiment.

To complete the description of components shown in FIG. 1, a field-illumination system 40 projects light onto the delivery axis 15, via a folding reflector 41 and a beam splitter 42, and a viewing device such as a stereo-observing biomicroscope 43 has a direct line of sight along axis 15. With both field stops 24, 34 adjusted to confine their respective beams to the same circular section, and with the two beam-displacement optics 25, 35 set for zero tilt (i.e., with their plane-parallel surfaces oriented normal to their respective optical axis 10, 11), the described system will deliver equal and coincident areas of radiation from both lasers A, B; if, on the other hand, one of stops 24, 35 is set for a larger beam-limiting section than the other, then delivered concentric overlap of radiation from the two lasers will be as depicted in FIG. 2, namely, with a central area 44 of concurrent response to both lasers, surrounded by a fringe annulus 45 of response to but one of the two lasers. The latter situation will be seen to have utility for a case wherein a buffer zone 45 of less-exposed tissue is desired between a central maximally treated zone and externally adjacent areas of untreated tissue.

As indicated generally above, it is the intention and purpose of the present invention to employ interaction between concurrent, or effectively concurrent, but dissimilar, laser beams of the character indicated to induce perturbations in affected micro-organisms whereby within tissue at the site of prospective surgery, the micro-organisms are destroyed, as a sterilizing procedure prior to surgical invasion. With the described apparatus, such dissimilarities are achieved through one or more of various combinations of beams on axes 10 and 11, as follows:

A. With identical lasers at A and B, as for example two He-Ne lasers, one on each of the axes 10, 11:
  (1) Adjust phase shifter 36, so that combined output on delivery axis 15 is sum of two spatially and temporally coherent radiations at identical wavelength, but phase-displaced with respect to each other.
  (2) Adjust polarization rotator 37, so that combined output on delivery axis 15 is the product of a predetermined difference in polarization-plane orientation for each of two spatially and temporally coherent radiations of identical wavelength.
  (3) Adjust the beam-displacement optics 24, 35 for equal and opposite offsetting displacements of their respective axes (from 10 to 10', and from 11 to 11', respectively) so that the beam 13a (15a) for laser-A radiation may be converted on a first axis 18a to treated tissue, and so that the beam 13b (15b) for laser-B radiation may be converged on a second axis 18b to the same area of treated tissue.
  (4) With a selected one of the modes (1), (2) or (3) above, operate the shutters (choppers) 21, 31 in synchronism, in accordance with a selected one of the following mode refinements:
    (a) shutter-open/shutter-closed, in coincident synchronism on both axes 10, 11.
    (b) shutter-open/shutter-closed, in time-interlaced relation on the respective axes 10, 11.
    (c) shutter-open action on one axis (1) in only partial cyclical overlap with shutter-open action on the other axis (11).
    (d) cyclical rate of less than 15 Hz, to allow affected-cell recovery between shutter-open exposures.
    (e) cyclical rate greater than 15 Hz, to suppress affected-cell recovery during period of treatment.

B. With non-identical lasers at A and B, as for example, a He-Ne laser on axis 10 and a krypton laser on axis 11:
  (5) Adjust attenuator 20 or 30 such that beam intensity at one wavelength on one axis (1) is equal to or greater than beam intensity at the other wavelength on the other axis (11).
  (6) Adjust polarization rotator 37, so that the combined output on delivery axis 15 is the product of a predetermined difference in polarization-plane orientation for each of two spatially and temporally coherent radiations of different wavelengths.
  (7) Adjust the beam-displacement optics 25, 35, for equal and opposite offsetting displacements of their respective axes (from 10 to 10', and from 11 to 11', respectively) so that the beam 13a (15a) for laser-A radiation may be converged on a first axis 18a to treated tissue, and so that the beam 13b (15b) for laser-B radiation may be converged on a second axis 18b to the same area of treated tissue.
  (8) With a selected one of the modes (5), (6), or (7) above, operate the shutters (choppers) 21, 31 in synchronism in accordance with one of the mode refinements recited in mode A (4) above.

Whatever the selected variety of laser at A or B, it is recommended that the combined intensity of beam energy deliverable to the affected area of body tissue be in the order of milliwatts/cm$^2$, as and preferably in the range of 600 to 6000 milliwatts/cm$^2$, depending upon the laser wavelength employed.

Figure 3:
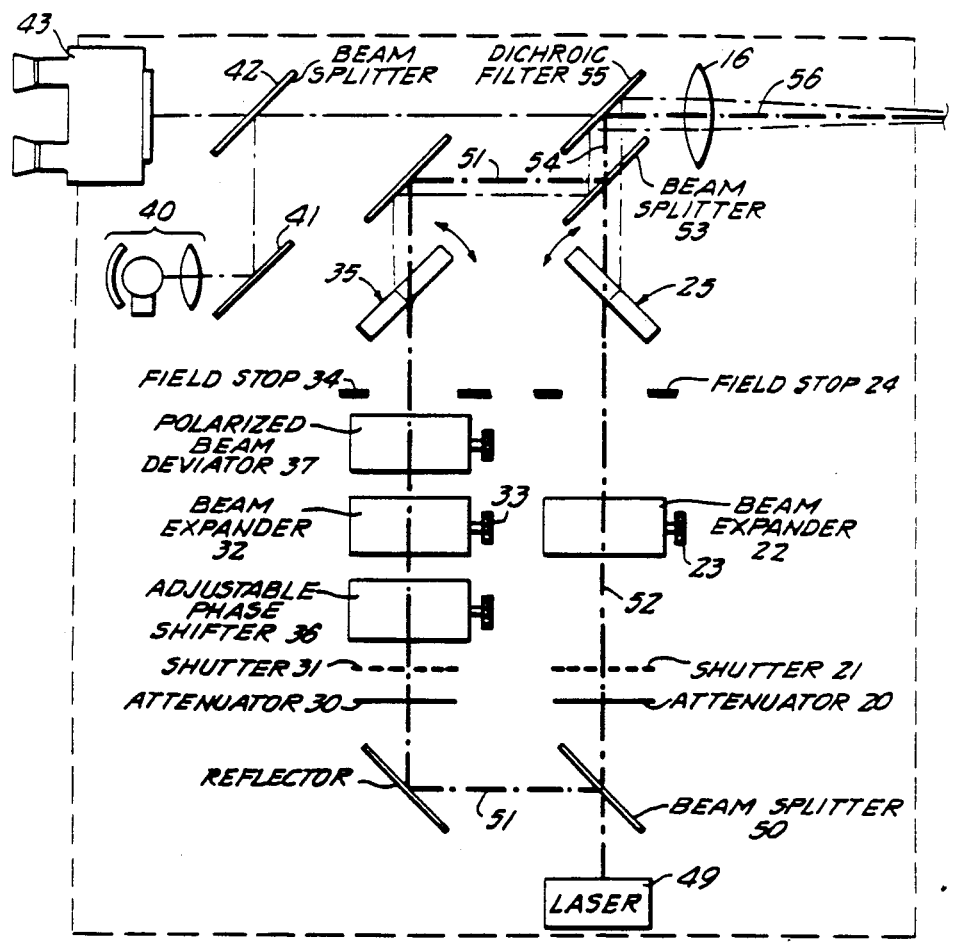
FIG. 3 is a diagram similar to FIG. 1 to show a modification.

In the embodiment of FIG. 3, the output beam from a single laser 49 is divided by a beam splitter 50 into beams 51, 52 on separate paths, which are thereafter recombined by beam-splitter means 53 to a single axis 54, before folding at a dichroic filter 55, to the delivery axis 56. Instrumentalities operative upon beam 52 are as described for the beam 10 from laser A in FIG. 1, and those operative upon beam 51 are as described for the beam 11 from laser B in FIG. 1; these instrumentalities, as well as illumination and viewing instrumentalities, have therefore been given the same reference numbers as in FIG. 1.

It will be seen that a single-laser embodiment of FIG. 3 is essentially the functional equivalent of the identical-laser situation mentioned above in connection with FIG. 1. The dissimilarities that may be produced in the divided beams 51, 52 of FIG. 3 may therefore include those tabulated under catagory A above for identical lasers on axes 10 and 11 of FIG. 1.

Figure 4:
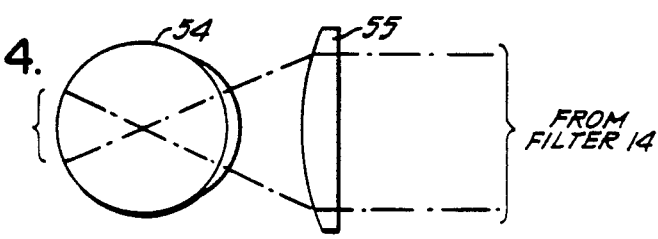
FIG. 4 is a simplified fragmentary optical diagram of one technique of laser-beam delivery, for either of the embodiments of FIG. 1 or FIG. 3.
Figure 5:
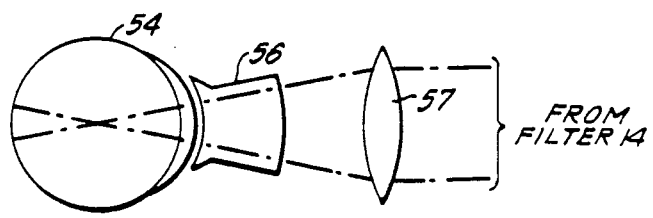
FIG. 5 is a similar fragmentary optical diagram of another technique of laser beam delivery, also for either of the embodiments of FIG. 1 or FIG. 3.

As to body-tissue application, the presently described multiple-beam exposures may be delivered either directly as a collimated beam wherein field-stop openings determine size and shape of a delivered spot or spots, or via a fiber-optic endoscope to an internal body-tissue region. For delivery within an eye 54, FIG. 4 illustrates use of a converging optic 55 to develop a relatively large area of exposure to the retina, while FIG. 5 illustrates use of a contact-lens element 56 in conjunction with a converging optic 57 to effect exposure over a more restricted area of the retina. It will be understood that beam cross-sectional areas delivered to the optic element 55 (or 56) will be determined by field-stop dimensional limitation, at legend-identified components of FIG. 1 or FIG. 3, as the case may be.

Parenthetic reference has been made above to choppers as having equivalence to shutters, for present purposes, with electrical or electronic control for their particular synchronized coordination; such controls are well understood and therefore need not now be described. It will also be understood that time-interlaced chopper action, as between two differently characterized laser beams delivered to body tissue, may be achieved by a rotary chopper having a flat mirror surface (1) that is inclined 45° to the one beam which is to be folded into axis alignment with that of the other beam, and (2) that the mirror surface is interrupted to provide an open sector space for non-reflected direct delivery of said other beam in interlace with reflected delivery of said one beam. In FIG. 1, such a mirror chopper is to be understood as symbolized by the 45°-inclined plane-parallel device called out as beam-splitter 12 in FIG. 1 or as beam-splitter 53 in FIG. 3.

It will further be understood that the operative limited spectral band of reflectivity at each of the dichroic filters 14 (55) will depend upon the particular selected lasers at A, B and 49. Thus, for HeNe and krypton lasers, the limited band of dichroic-filter reflectivity is suitably 610 to 660-nm, thereby allowing for field illumination (from 40) and viewing (from 43) via a generous remainder of the visible spectrum.

For an understanding of use of the described apparatus for laser aseptic phototherapy, as in connection with sterilizing an area of body tissue prior to surgical invasion, it is helpful to observe that the time-honored technique involves chemical and mechanical scrubbing of the superficial layers of the epidermis, using such agents as iodine, alcohol and several other components (e.g., Phisohex) to chemically obliterate microorganisms on the remaining surface. But none of such antiseptic agents is effective deep in the area of hair follicles or crypts that extend deep into the dermis and that harbor considerable amounts of bacteria and/or other pathologicorganisms, e.g., viruses, chlamydia. Such bacteria can be massaged to the surface within minutes after initial preparation of the incision site, but bacterial removal by such a technique is not always complete, in which case post-operative infection can occur.

Figure 6:
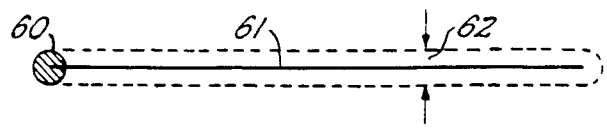
FIG. 6 is a diagram in aid of discussion of a presurgery use of the invention.

The invention proposes to utilize the described apparatus to deliver direct irradiation of specific wavelength, with penetration deep into the dermal layers, such irradiation to be used alone or in conjunction with (i.e., as a back-up for) conventional antiseptic techniques. Furthermore, the oral use of a photosensitizing agent such as tetracycline compound or a small intravenous injection of hematoporphyrin derivative (HpD) is recommended several hours (e.g., 6 to 8 hours) before the time of surgery, with a view to potentiating the action of a particular wavelength. Such a delay allows washout of the HpD from normal cells, while more highly metabolic cells such as bacteria, and in particular bacteria in the follicles and crypts, become the seats of relatively great absorption of photosensitive agent; thus, after the delay period and immediately prior to surgery, irradiation with above-described laser means having a wavelength known to be most highly absorbed by the administered photosensitizing substance can then cause the thermal or photochemical death of the potentially infectious organisms deeply situated within the skin. Illustratively, with a 1-cm circular spot 60 (FIG. 6) at focus of the exit beam on axis 15 (FIG. 1) or on axis 56 (FIG. 3), and with a prospective surgical line 61 of incision 10-cm long, laser irradiation can do the job of killing the deep-seated bacteria in a continuous 30-second sweep of the circular spot along the prospective line of the incision—i.e., at a sweep speed of approximately 3 seconds per unit area of the 1-cm wide swath 62 traversed in the course of the sweep. In this connection, it is recommended that an articulated arm be used (as suggested by legend in FIG. 1) for laser-beam delivery to the situs of surgery, thus allowing the surgeon the freedom needed for optimum orientation of the laser beam in the course of making the described sweep.

The indicated technique of laser aseptic phototherapy can also be applied to mucous membranes, and other body regions such as the gums, where an incandescent or laser-light source can be applied to the affected gum region directly, or after an oral, intravenous, or mouthwash type of prephotosensitization of involved organisms. Following the sensitization, the gum or mucous membrane region thought to be infected should be irradiated for a short period of time with a wavelength highly absorbed by the photosensitizing substance and at a power density sufficient to cause death of the microorganisms. Specifically, for treatment of gingivitis, it is recommended to use a mouthwash to stain areas of spirochetes and bacteria, prior to irradiation of the stained areas.

Mention has been made above, indicating that tetracycline or hematoporphyrin ether are satisafactory sensitizing agents. A tetracycline use (capsule, taken orally) is suitably followed by argon-laser irradiation, at about 500 nanometers. A hematoporphyrin ester/ether (DHE) use, is used topically or intravenously, and is suitably followed by He-Ne-laser or dye-laser irradiation, at 632.8 nanometers, or argon-laser irradiation with laser emissions around 500-nm. Chlorophyll and associated compounds, applied topically, orally, or intravenously, are also suitably followed by organicdye laser irradiation from a highly absorbed laser emission, as is also the case of phthalocyanines, other porphyrins, dihydroporphyrins ($\lambda_{max}$. 670–690-nm) and tetrahydroporphyrins ($\lambda_{max}$. 750–820-nm) In general, a 10-milliwatt beam intensity, at sufficient power density, will suffice for laser aseptic phototherapy with certain human tissue. And noting that a 5-milliwatt HeNe laser is generally available at reasonable cost, compared to the very much greater cost of, say, a 15-milliwatt HeNe laser, it makes good sense to employ separate 5-milliwatt HeNe lasers at the locations A-B of FIG. 1, rather than use of a single larger and much more expensive 15-mw HeNe laser in the arrangement of FIG. 3; in using the two 5-mw HeNe lasers in FIG. 1, a desired 10-mw output is achieved merely by correct adjustment of phase shifter 36 until the respective laser outputs are in phase coincidence, once combined at phase-splitter 12. Such tandem or plural use of like lasers is also applicable to other laser sources, and to variations in required power density, depending upon the tissue irradiated.

For convenience, the wavelength (in nanometers) of maximum absorption of above-mentioned and other suggested photosensitizing agents is tabulated below:

| Photosensitizing Agent | Wavelength (λ) at Maximum Absorption (nm) | Recommended Laser for Maximum Absorption |
|---|---|---|
| Hematoporphyrin derivative | 500.0 or 630.0 | Argon (500) or Dye (630) Laser |
| Dihematoporphyrin ether/ester (DHE) | 500.0 or 630.0 | Argon (500) or Dye (630) Laser |
| Tetracycline | 500.0 | Argon Laser |
| Acridine orange | 539.0 | Frequency-doubled Neodymium-YAG Laser |
| Trypan blue | 585.0 | Organic-Dye Laser |
| Evan's blue | 610.0 | Organic-Dye Laser |
| Methylene blue | 665.0 | Organic-Dye Laser |
| Indocyanin green | 800.0 | Diode Laser |
| Phthalocyanines | 670.0–700.0 | Organic-Dye Laser, or Diode Laser |
| Chlorophyll | 660–680 | Organic-Dye Laser |

It is understood that the above-described combinations are merely illustrative of the many possible specific embodiments which respresent applications of the present invention. Numerous and varied other arrangements can readily be devised in accordance with the principles of the present invention without departing from the spirit and scope thereof.

What is claimed is:

1. The method of preparing an area of living tissue for surgical invasion, by destroying infective target micro-organisms within said area, said method comprising irradiating said area with first and second separate laser beams of intensity and wavelength selected for interaction with said target micro-organisms, each of said beams having properties of spatial and temporal coherence, and said beams having different physical properties at tissue impingement within said area, wherein the difference is in respect of at least one physical property the combined power of said beams being at least 10 milliwatts and the intensity of said beams being less than sufficient to induce photocoagulation, photovaporization, photonoptical breakdown or photoablative decomposition of living tissue and/or cells, whereby within said area to effect intra-micro-organism changes leading to destruction in the micro-organism.

2. The method of claim 1, in which the combined intensity of said beams is no greater than 6,000 milliwatts/cm$^2$.

3. The method of claim 1, in which the wavelength of each of said laser beams is at least 400 nanometers.

4. The method of claim 1, in which said beams are of the same wavelength but converge for tissue impact from different aspects.

5. The method of claim 1, in which said beams are of the same wavelength but in phase-offset relation to each other.

6. The method of claim 1, in which said beams are of the same wavelength and are in polarization-coincidence and phase-coincidence with each other.

7. The method of claim 1, in which said beams are of the same wavelength and are polarized in mutually offset planes.

8. The method of claim 1, in which said first beam impacts body tissue over an area greater than but fully overlapping the area of tissue impact by said second beam.

9. The method of claim 1, in which said beams are delivered for tissue impact in chopped interlace.

10. The method of preparing an area of living tissue for surgical invasion, which method comprises administering a photosensitizing agent which in the course of a predetermined subsequent period of time becomes selectively absorbed primarily in the situes of micro-organisms at depth within the tissue, allowing the lapse of said period of time, then irradiating said area with at least one beam of laser radiation of intensity and wavelength selected for absorption at loci of photosensitizing-agent concentration in said area, thereby destroying agent-absorbing micro-organisms within and beneath said area, said intensity being less than sufficient to induce photocoagulation, photovaporization, photonoptical-tissue breakdown or photoablative decomposition of living tissues and/or cells, the power of said beam being at least 10 milliwatts, and said intensity being no greater than 6,000 milliwatts/cm$^2$.

11. The method of claim 10, in which the intensity of beam energy delivery to the area of body-tissue impact is in the range of 600 to 6000 milliwatts/cm$^2$.

12. The method of claim 10, in which the wavelength of said laser radiation is at least 400 nanometers.

13. The method of claim 10, in which said laser radiation is the product of combined delivery of two laser radiations directed to the same area of tissue impact.

14. The method of claim 13, in which said radiations differ physically in at least one respect.

15. The method of claim 13, in which said radiations are of the same wavelength but converge for tissue impact from different aspects.

16. The method of claim 13, in which said radiations are of the same wavelength but in phase-offset relation to each other.

17. The method of claim 13, in which said radiations are of the same wavelength and are in polarization-coincidence and phase-coincidence with each other.

18. The method of claim 13, in which said radiations are of the same wavelength and are polarized in mutually offset planes.

19. The method of claim 13, in which one of said two radiations impacts body tissue over an area greater than but fully overlapping the area of tissue impact by the other of said two radiations.

20. The method of claim 13, in which said radiations are of different wavelength, the wavelength of at least one of said radiations being selected for absorption response by the photosensitizing agent.

21. The method of claim 20, in which said radiations are delivered for tissue impact in chopped interlace.

22. The method of claim 10, in which the administering of a photosensitizing agent includes the step of selecting said agent from the group comprising porphyrins, dihydroporphyrins, phtalocyanines, tetrahydroporphyrins, and cationic dyes.

23. The method of claim 10, in which the administering of a photosensitizing agent includes the step of selecting said agent from the group comprising tetracycline, acridine orange, trypan blue, Evans' blue, methylene blue, and indocyanin green.

24. The method of claim 10, in which the administering of a photosensitizing agent includes the step of selecting a photosensitizing agent which contains chlorophyll as an essential component.

25. Biomedical sterilizing apparatus for local destruction of micro-organisms in body tissue prior to surgical invasion, comprising laser means for producing two beams of laser radiation, to a single local area of impact with body tissue and interaction with micro-organisms within said local area, said beams differing physically in at least one respect and having a combined power which is at least 10 milliwatts and which is less than 6000 milliwatts/cm$^2$ and less than sufficient to induce photocoagulation, photovaporization, photonoptical breakdown or photoablative decomposition of living tissue and/or cells.

26. Biomedical sterilizing apparatus according to claim 25, in which said laser means comprises two lasers, and means including a beam splitter for combining the beams from said lasers for coordinated delivery to said local area.

27. Biomedical sterilizing apparatus according to claim 25, in which said laser means comprises a single laser producing a single beam, and means including a beam splitter in the path of said single beam for dividing the same into said first and second output beams.

28. Biomedical sterilizing apparatus according to claim 25, in which said laser means comprises a first laser producing said first output beam at a first wavelength, and a second laser producing said second output beam at a second wavelength.

29. Biomedical sterilizing apparatus according to claim 27, in which said laser means is a helium-neon laser.

30. Biomedical sterilizing apparatus according to claim 27, in which said laser means is a krypton laser.

31. Biomedical sterilizing apparatus according to claim 26, in which at least one of said lasers is a diode laser.

32. Biomedical sterilizing apparatus according to claim 25, in which said laser means comprises two lasers, and means including a mirror chopper for combining the beams from said lasers in chopped interlace.

33. Biomedical sterilizing apparatus according to claim 25, in which delivery of at least one of said beams is with spatial and temporal coherence.

34. Biomedical sterilizing apparatus according to claim 25, in which delivery of each of said beams is with spatial and temporal coherence.

35. Biomedical sterilizing apparatus according to claim 25, in which said beams are of identical wavelength but in phase-offset relation to each other.

36. Biomedical sterilizing apparatus according to claim 25, in which said beams differ physically in respect of polarization.

37. Biomedical sterilizing apparatus according to claim 25, in which means including a mirror chopper combines said beams for delivery in chopped interlace.

38. Biomedical sterilizing apparatus according to claim 25, in which said beams converge from different aspects for overlapping delivery at said area.

* * * * *